US012599356B2

(12) United States Patent
Radhakrishnan et al.

(10) Patent No.: US 12,599,356 B2
(45) Date of Patent: Apr. 14, 2026

(54) FETAL HEART RATE MONITORING

(71) Applicant: KONINKLIJKE PHILIPS N.V., Eindhoven (NL)

(72) Inventors: Ravindranath Radhakrishnan, Bangalore (IN); Pallavi Vajinepalli, Bangalore (IN); Hansjoerg Geywitz, Eindhoven (NL); Hoa Pham, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/838,731

(22) PCT Filed: Feb. 7, 2023

(86) PCT No.: PCT/EP2023/052887
§ 371 (c)(1),
(2) Date: Aug. 15, 2024

(87) PCT Pub. No.: WO2023/156243
PCT Pub. Date: Aug. 24, 2023

(65) Prior Publication Data

US 2025/0213212 A1 Jul. 3, 2025

(30) Foreign Application Priority Data

Feb. 15, 2022 (EP) .................................... 22156815

(51) Int. Cl.
*A61B 8/02* (2006.01)
*A61B 8/00* (2006.01)
*G06T 7/00* (2017.01)

(52) U.S. Cl.
CPC .............. *A61B 8/02* (2013.01); *A61B 8/4245* (2013.01); *A61B 8/4483* (2013.01); *A61B 8/461* (2013.01);
(Continued)

(58) Field of Classification Search
CPC ....... A61B 8/02; A61B 8/4245; A61B 8/4483; A61B 8/461; A61B 8/488; A61B 8/5215;
(Continued)

(56) References Cited

U.S. PATENT DOCUMENTS 3,561,430 A * 2/1971 Filler, Jr. ................ A61B 8/02 600/407
10,849,599 B2 * 12/2020 Song ..................... G16H 30/40
(Continued)

FOREIGN PATENT DOCUMENTS

CN 109330626 A 2/2019
CN 112168210 A 1/2021
(Continued)

OTHER PUBLICATIONS

International Search Report Dated May 8, 2023 For International Appln No. PCT/EP2023/052887 Filed Feb. 7, 2023.
(Continued)

*Primary Examiner* — Bo Joseph Peng

(57) ABSTRACT

The invention relates to an ultrasound fetal heart rate monitoring system (100). An ultrasound probe placed on a maternal abdomen provides sensor data. The ultrasound probe is first operated in an imaging mode to obtain an ultrasound image from the ultrasound probe. A trained object detection model is applied to the ultrasound image to determine whether a fetal heart is located in a target region of the ultrasound image addressable by a Doppler mode of the ultrasound probe. If the fetal heart rate is located in the target region, the ultrasound probe is switched to the Doppler mode; a Doppler ultrasound signal is obtained from the ultrasound probe; and the fetal heart rate is computed from the Doppler ultrasound signal.

14 Claims, 5 Drawing Sheets

(52) U.S. Cl.
CPC ............ *A61B 8/488* (2013.01); *A61B 8/5215* (2013.01); *A61B 8/54* (2013.01); *G06T 7/0012* (2013.01); *A61B 2562/028* (2013.01); *G06T 2207/10132* (2013.01); *G06T 2207/20081* (2013.01); *G06T 2207/30012* (2013.01); *G06T 2207/30044* (2013.01); *G06T 2207/30048* (2013.01)

(58) Field of Classification Search
CPC ... A61B 8/54; A61B 2562/028; A61B 8/0866; G06T 7/0012; G06T 2207/10132; G06T 2207/20081; G06T 2207/30012; G06T 2207/30044; G06T 2207/30048
See application file for complete search history.

(56) References Cited

U.S. PATENT DOCUMENTS

| | | | | |
|---|---|---|---|---|
| 11,766,236 | B2* | 9/2023 | Park | A61B 8/5207 600/443 |
| 2005/0251036 | A1* | 11/2005 | Abuhamad | A61B 8/0866 600/443 |
| 2013/0158407 | A1* | 6/2013 | Kabakov | A61B 8/0866 600/453 |
| 2013/0190600 | A1* | 7/2013 | Gupta | A61B 8/0866 600/407 |
| 2015/0190112 | A1* | 7/2015 | Yeo | A61B 8/0883 600/443 |
| 2016/0213349 | A1* | 7/2016 | Groberman | A61B 8/02 |
| 2016/0242732 | A1* | 8/2016 | Strassner | A61B 8/461 |
| 2018/0015350 | A1 | 1/2018 | Lindsay | |
| 2019/0133549 | A1 | 5/2019 | Hamelmann | |
| 2020/0069285 | A1 | 3/2020 | Annangi | |
| 2020/0113542 | A1* | 4/2020 | Perrey | A61B 8/4254 |
| 2020/0261053 | A1* | 8/2020 | Park | A61B 8/5207 |
| 2021/0161508 | A1* | 6/2021 | Schadewaldt | A61B 8/0883 |

FOREIGN PATENT DOCUMENTS

| | | | |
|---|---|---|---|
| CN | 112773402 | A | 5/2021 |
| EP | 3454758 | B1 | 8/2019 |
| JP | 2018134386 | A | 8/2018 |

OTHER PUBLICATIONS

M. N. Senlik and H. Koymen, “Radiation Impedance of an Array of Circular Capacitive Micromachined Ultrasonic Transducers”, IEEE Transactions on Ultrasonics, Ferroelectrics, and Frequency Control, vol. 57, No. 4, Apr. 2010.
J. Redmon et al., “You Only Look Once: Unified, Real-Time Object Detection” (available at https://arxiv.org/abs/1506.02640 and incorporated herein by reference).
Hannes Hase et al: “Ultrasound-Guided Robotic Navigation with Deep Reinforcement Learning”, Apr. 7, 2020.

* cited by examiner

FETAL HEART RATE MONITORING

CROSS-REFERENCE TO PRIOR APPLICATIONS

This application is the U.S. National Phase application under 35 U.S.C. § 371 of International Application No. PCT/EP2023/052887, filed on Feb. 7, 2023, which claims the benefit of International application Ser. No. 22/156,815.7 filed on Feb. 15, 2022. These applications are hereby incorporated by reference herein.

FIELD OF THE INVENTION

The invention relates to an ultrasound fetal heart rate monitoring system, and to a corresponding computer-implemented ultrasound fetal heart rate monitoring method. The invention further relates to a computer-readable medium.

BACKGROUND OF THE INVENTION

Complications during labor and delivery can have an impact on the safety of both mother and new-born. There are about 500,000 maternal deaths arising from complications during childbirth every year, around the world. About 7 million women have major long-term problems after giving birth and 50 million women face a negative impact on their health after giving birth.

The fetal heart rate is an important piece of information for evaluating the fetal well-being during labor and delivery. Today, for this purpose, typically fetal monitors based on Doppler ultrasound are used. The Doppler effect may be used to calculate the fetal heart rate, based on a measured frequency shift. The fetal heart rate may be measured using multiple ultrasound transducer elements based on the power of the received Doppler signals in the elements.

Unfortunately, existing fetal monitors are complicated and time-consuming to use, in particular due to the manual (re-)positioning of the transducers of the fetal monitor. It is important for the reliability of fHR measurements that the fetal heart is located within the ultrasound beam. In clinical practice, clinicians palpate the maternal abdomen to identify the fetal presentation and then the ultrasound transducer is fixated on the maternal abdomen where the best fHR signal can be obtained. Finding the optimal transducer position is done based on listening to the strength of the Doppler audio output and/or based on signal quality indicators. Due to displacement of the ultrasound transducer or displacement of the fetal heart out of the ultrasound beam, the fHR signal may be lost. Therefore, it is often necessary that the obstetrician repeats the tedious procedure of ultrasound transducer positioning to avoid long periods of fHR signal loss. Moreover, it is a disadvantage that the person using the equipment needs to be well trained, especially since there is a risk that the maternal heart rate (e.g., captured from the umbilical cord or other maternal vessels) gets picked as the fetal heart by the fetal monitor.

European patent EP 3454758 B1 discloses a method for determining an optimal position of an ultrasound transducer during fetal health monitoring. An ultrasound device is used that has a central piezoelectric element and additional piezoelectric elements arranged in a circle around it. The device supports a position support mode and a fetal heart rate mode. In the position support mode, one element of the transducer is used to generate an ultrasound signal, and ultrasonic echoes of the signal are received at the respective elements to determine respective Doppler signals. The user is notified which transducer has the strongest Doppler signal strength, thus assisting the user to reposition the device such that the central element has the strongest signal. In the fetal heart rate mode, all piezoelectric elements are used both for transmission and for reception to create an overall Doppler signal of the fetal heart rate.

SUMMARY OF THE INVENTION

It would be beneficial to provide a system for fetal heart rate monitoring that better helps to ensure correct placement of the used ultrasound probe, for example for unexperienced users such as during home monitoring.

In accordance with a first aspect of the invention, an ultrasound fetal heart rate monitoring system and a corresponding method are provided. In accordance with a further aspect of the invention, a computer-readable medium is provided.

Various aspects relate to monitoring a fetal heart rate by using an ultrasound probe to obtain a Doppler ultrasound signal. The Doppler ultrasound signal may be indicative of the frequency shift of a measurement volume. Based on this frequency shift, the fetal heart rate may be determined. In particular, as is known per se, by determining the speed and/or direction of movement of the heart's wall, the fetal heart rate may be determined. In most cases, the Doppler ultrasound signal is obtained in a so-called pulsed wave (PW) Doppler mode. In PW Doppler mode, multiple pulses may be transmitted, and relative phase changes of the transmitted pulses may be used to derive a frequency shift and thereby the speed and/or direction. As an alternative to using PW Doppler, it is also possible to use continuous wave (CW) Doppler. In CW Doppler, sound waves may be continuously transmitted and received, allowing to record respective velocities along a defined path.

To make sure that the Doppler ultrasound signal indeed represents a measurement of the fetal heart, and not for example the pulsation of a maternal vessel, the inventors envisaged to use an ultrasound probe that can also be operated in an imaging mode to obtain an ultrasound image. In particular, unlike the probes that are typically used for Doppler ultrasound, the probe may be equipped with a phased array of transducers, for example a 1D or 2D phased array. The ultrasound image data may be input to an object detection model to determine whether the fetal heart is located in a target region of the ultrasound image that is addressable by the Doppler mode of the ultrasound probe. The imaging mode can for example be a so-called B-mode (brightness mode), also known as 2D mode. For example, a 1-dimensional phased array of transducers may be used to scan a plane through the measurement volume, thereby obtaining a 2D ultrasound image, in other words, a 2D ultrasound scan frame.

Although ultrasound imaging is known per se, today it is not widely used in the active phase of labor, because it generally requires high training effort to operate, including acquiring and interpreting the data, and because, the current form-factor is not suitable for monitoring purpose. However, the inventors found that, by using ultrasound imaging determine whether the fetal heart is located in a target region, it can still be advantageously used in the context of Doppler-based fetal heart rate monitoring.

The trained object detection model may be applied to the ultrasound image obtained in the imaging mode. The object detection model may be configured to localize a fetal heart in an ultrasound image, e.g., to output a location of the fetal heart in the ultrasound image, if detected, or to output that the fetal heart was not detected at all. If the detected location falls within a certain target region, the ultrasound probe may be switched to the Doppler mode to measure the fetal heart rate, e.g., by using one of the transducers of the phased array that is also used for the imaging, as described above.

The provided approach has a number of advantages. Because of the use of a trained object detection model applied to an ultrasound image, the fetal heart can be localized with high reliability. As a consequence, the fetal heart rate measured when switching to the Doppler mode upon the fetal heart being recognized, is more likely to be accurately measured as well. Using the ultrasound image allows the imaging capability of ultrasound sensors to be exploited. With this newly available visual information, modern object detection models such as convolutional neural networks may be exploited. Object detection techniques can provide excellent performance, and can run on modest hardware in real-time, or near-real-time. One reason for the improved accuracy is that the object detection model works on an ultrasound image and not on a Doppler signal. This means that, in order to localize the fetal heart, e.g., even for midterm progress of the delivery, the model can use other parts of the anatomy of the maternal abdomen and/or the fetus. For example, the fetal spine or femur may be visible in the ultrasound image, unlike in Doppler data. Even when the object detection model is only trained to recognize the fetal heart, it can implicitly use this other information as well.

Also, because the recognition is visual and not based on a Doppler signal, the risk of confusing the fetal heart with other sources that produce a Doppler signal is eliminated. When relying on the strongest Doppler signal strength, this by itself does not guarantee that the fetal heart is being measured and not another anatomy that produces a Doppler shift in the wanted base band. Since the visual recognition is independent of the fetal heart itself or Doppler shifts produced by any other vessel, its accuracy and therefore also its safety are improved.

Another advantage is that localization can be obtained even if the fetal heart is not in focus of the beam at all. For example, a measurement volume of an ultrasound probe in Doppler mode may be a cylindrical area of around 10 cm wide. Providing guidance based on Doppler ultrasound may be effective if the fetal heart is close to that measurement volume, e.g., within 20 cm. Further away, techniques based on Doppler have a particularly high risk of recognizing other anatomic parts than the fetal heart or otherwise providing ambiguous guidance, whereas a localization based on imaging is still effective. For example, imaging-based localization can be effective based on an initial placement of the probe anywhere on the abdomen. For example, the probe may be placed at two positions within a relatively short period of time and then be told the best position for measuring the fetal heart, even if those positions are not where the fetal heart itself is located.

Moreover, the use of an image detection model applied in an imaging mode has a number of additional advantages as well, related to the fact that, while in imaging mode, the system may output the ultrasound image and/or the location. These outputs can be used in various ways, as also described elsewhere, e.g., to detect other parts of the fetal anatomy to provide guidance even when the fetal heart is not visible; to show the image and/or the location; and/or to focus the Doppler ultrasound.

Compared to using the probe in imaging mode only, the use of Doppler mode for measuring the fetal heart rate has a number of advantages. One advantage is that existing reliable measurement techniques for the Doppler mode can be used. Moreover, Doppler mode may use a lower amount of power than imaging mode. For example, Doppler mode may use less than 20 mW/cm^2, whereas imaging mode may use more than that. As a consequence of the reduced power consumption, the system may be more suitable for continuous monitoring, e.g., the system may be used for monitoring for at least one hour, for at least four hours, or for at least ten hours. Especially during such prolonged use, using less power, e.g., less than 20 mW/cm^2, helps to prevent damage to bone skin. Also the heat produced by the device may be reduced due to the lower power, making the device feel more comfortable on the abdomen and improving the lifetime of the device's components.

The same transducers may be used both to capture the ultrasound image and the Doppler ultrasound signal, e.g., the Doppler ultrasound signal may be captured by one of the transducers also used for the imaging. This way, a relatively small amount of hardware may suffice, and it is ensured that locations of the ultrasound image in imaging mode coincide with addressable regions of the ultrasound sensor in Doppler mode, since the used transducers are in both cases the same.

The target region for switching to the Doppler mode can coincide with the full ultrasound image but is preferably a subregion of the full ultrasound image, e.g., a subregion that excludes border regions of the ultrasound image, e.g., excludes at most or at least 10%, at most or at least 20%, or at most or at least 30% of the imaged region. This way, it may be prevented that if the probe is switched to the Doppler mode, and then slightly moved so that the signal lost, and then switched back to the imaging mode, the fetal heart is out of reach of the ultrasound sensor. The region addressable by the ultrasound probe in Doppler mode may in many cases coincide with the region captured by the ultrasound image, e.g., the full image may be addressable in Doppler mode. Also in such cases, the target region for which the device switches to Doppler mode, is typically a subregion of this full region that can be imaged and/or Doppler-measured.

Optionally, when in Doppler mode, a signal quality indication of the Doppler ultrasound signal may be determined e.g., using known techniques. If the signal quality indication does not meet a predefined quality threshold, the ultrasound probe may be switched back to the imaging mode, e.g., the object detection model may again be repeatedly applied until the fetal heart is localized. Thus, it may be further ensured that the measured fetal heart rate is accurate; in imaging mode, the fetal heart rate may not be measured until the fetal heart is in a desired target region; in Doppler mode, the signal quality indication may ensure sufficient quality for an accurate measurement of the heart rate. The quality threshold may be calibrated such that, at least if the fetal heart is in the target region, the signal quality is generally sufficient. It is possible to have a stricter definition of the target region, however, e.g., the signal quality may be sufficient also outside of the target region. The opposite situation where the signal quality is insufficient even if the fetal heart is in the target region, is however generally not desired.

In any case, it is preferred that the quality threshold is threshold is calibrated in such a way that the threshold generally lies in the region captured by the ultrasound image, e.g., including a safety margin. This way it is possible to, when the threshold is reached, automatically switch to imaging mode for the fetal heart to be recognized, and possibly to automatically switch to Doppler mode again using an updated position on which the Doppler ultrasound beam may be focused, e.g., by beamsteering, without the need to reposition the probe.

Optionally, the signal quality indication may be output in a sensory-perceptible way to a user. This way, the user may be informed if the probe is in a good location on the abdomen, and the user can try to move the probe to improve the signal quality. It is particularly convenient for the user to use a visual indicator, e.g., one or more lights, on the ultrasound probe itself.

Optionally, the ultrasound probe comprises one or more transducers in the form of piezoelectric transducers and/or capacitive micromachined ultrasonic transducers (CMUT). For example, the transducers may form a phased array of multiple transducers, e.g., a linear phased array, allowing to generate a 2D ultrasound image. The transducers can also form a grid, e.g., a matrix array, of transducers, allowing to generate a 3D ultrasound image.

Optionally, the Doppler ultrasound beam may be focused on the located position. In other words, a window for the Doppler measurement, which may include the depth, may be set according to the located position. Various ultrasound probes, in particular ones based on transducer arrays, support the use of beamforming to focus the Doppler ultrasound beam to a particular location. Focusing is particularly advantageous in combination with the use of object detection to determine a location of the fetal heart, since the ultrasound beam can then be focused to that particular location. For example, the fetal heart may not need to be located in a cylindrical column directly below the ultrasound probe as can be the case for some prior art techniques. This makes the ultrasound particularly easy to use, e.g., also with little or no training, since the placement of the ultrasound probe needs to be a lot less exact.

Compared to using depth selection, a number of advantages are provided. Focusing the Doppler ultrasound beam may involve setting not (only) the depth, but also horizontal and vertical positions perpendicular to the depth. Only setting the depth has the advantage that this cannot deal with the situation where there is more than one signal source in this depth region. Moreover, depth selection needs a good initial signal to focus on the depth, whereas the provide techniques may even provide guidance information if the fetal heart is not in the imaged region. The provided techniques also remedy the slow, iterative window setting of depth selection, and do not have the problem that once the signal to noise ratio gets worse, the window is opened completely.

Optionally, the ultrasound image and/or the position of the fetal heart in the ultrasound image may be shown on a display. For example, the ultrasound image, or a diagrammatic image of a maternal abdomen, e.g., an avatar, may be shown, with a box, cross, or similar being used to indicate the detected position. This can serve several purposes. It can help guidance of the ultrasound probe, since the user can see on the screen where the fetal heart is located with respect to the picture produced by the ultrasound prove and so also with respect to the probe itself.

Optionally, the ultrasound image itself is not shown on the display. Showing e.g., a diagrammatic image instead of the ultrasound image itself may allow easier interpretation, and may also be preferred in cases where the user is for example not permitted for legal reasons to see and/or judge on the ultrasound image itself, or where the mother does not want this image to be seen, for example. The ultrasound image may be processed in the background but not stored or shown to the user. Optionally, the target region for switching to the Doppler mode may be visualized as well, providing guidance to the user on when a switch to Doppler mode can be expected.

When showing the ultrasound image itself, the displaying of the position where the fetal heart is detected can also be used as a reliability mechanism, by allowing the user to check whether the system has correctly recognized the fetal heart. For example, when the system has switched to Doppler mode and/or has used the recognized fetal heart to focus the Doppler ultrasound beam, the user can verify whether this is based on correct recognition of the heart.

Optionally, the object detection model is configured to localize one or more fetal body parts of the fetus in addition to the fetal heart. These body parts can include the head, spine, and/or femur of the fetus. The fact that ultrasound imaging is used instead of Doppler signals, allows these body parts to be recognized as well. Outputting these additional localizations is advantageous because this information can make it easier to locate the ultrasound probe at the correct location, in particular also in situations where the fetal heart itself is not visible in the image.

One way of outputting the additional localizations is to show them on a display, e.g., the ultrasound image may be shown together with localizations of any fetal body parts that the object detection model is configured to localize. These localizations may help the user, especially inexperienced users such as nurses or midwives, to determine the orientation of the fetus and thereby to locate the ultrasound probe to operate it properly.

Another way to use localizations, at least of the fetal heart but possibly also any other fetal body parts that the object detection model may be configured to localize, is to determine guidance information for guiding the ultrasound probe to the fetal heart. This guidance information can be output to a display. Interestingly, the guidance information can suggest to move the probe to a different location on the maternal abdomen, as opposed to just suggesting to rotate or change the angle of the probe with respect to the abdomen.

In particular, the guidance information may be based on localizations of one or more of the fetal head, the fetal spine, and the fetal femur. In particular, if the fetal spine is detected and the fetal head is not detected, guidance information may be determined for guiding the ultrasound probe to an expected location of the fetal head. This is beneficial because the fetal spine can be oriented in any position in the uterus, making successful placement less dependent on the initial placement of the probe. Moreover, the location of the fetal spine is greatly informative of the overall anatomy of the fetus. Given the location of the spine, it is possible to suggest a location of the fetal heart and so a placement of the ultrasound probe to capture it. Also locating the fetal head is beneficial since it can be recognized relatively reliably and, once the ultrasound probe is placed at the location of the fetal head and both the fetal head and fetal spine are detected, it is possible to particularly reliably suggest guidance to the fetal heart. Guidance information may then be determined for guiding the ultrasound probe to an expected location of the fetal heart.

To determine the guidance information, an algorithm can for example be used that internally reconstructs the geometry of the fetus based on the localizations. It is also possible to use a machine learnable guidance model that is e.g., trained to output the guidance based on a labelled dataset.

The guidance information can be presented in various ways, e.g., visualized as a suggested location on a grid, for example augmented on an image of a maternal abdomen, for example a 3-by-3 grid or similar. Examples are given herein. The guidance information may be combined with a visualization of a determined fetal anatomy and/or with actual images from the ultrasound probe, as desired. The guidance information may be shown without showing (and possibly without storing) the actual ultrasound image, which, as also mentioned elsewhere, can make the visualization easier to interpret and which is useful in situations where it is not desired to show the ultrasound image.

Guidance based on localizations of body parts is a particularly effective guidance mechanism, that moreover has the added advantage that the overall placement of the fetus can be determined and not just the location of the fetal heart per se. Moreover, this type of guidance may be familiar to people accustomed to clinical practice, in which the person placing the ultrasound probe typically follows a protocol where the clinician palpates the maternal abdomen according to a fixed pattern, e.g., upper side→lower side→left side→right side, to uncover the anatomy of the fetus. Such a protocol as is used today may in practice take 15-20 minutes even for an experienced person. The provided guidance techniques allow to bring down this time significantly, and may allow the probe to be also used by inexperienced or non-certified users (nurses, midwives) during birth management. Although the system may, upon detecting the spine, aim to first guide the probe to the head and then to the heart, if the heart is detected sufficiently reliable already in the meantime, it is possible to directly switch to Doppler mode upon this detection. It is however also possible to only detect the fetal heart and/or switch to Doppler mode after both the spine and the head have been detected, e.g., to allow the fetal orientation to be fully determined prior to switching modes.

Optionally, the orientation of the ultrasound probe may be used to determine the guidance information. For example, the ultrasound probe may comprise an inertial measurement unit (IMU) providing an orientation angle of the ultrasound probe. The orientation may be input to the object detection model to determine the location of the fetal heart and/or other body parts, and can also be used to determine the guidance information, interestingly, given the sphere-like shape of the maternal abdomen, the orientation of the ultrasound probe can provide a reasonably accurate estimate of the location of the ultrasound probe on the abdomen, and so can be used as an input representing the current location of the probe, in particular to determine guidance but also as an input to the object detection model.

The above aspects relate to systems and methods that use a machine learnable object detection model and/or guidance model. Also envisaged is a system for training an object detection model and/or guidance model for these uses, and a corresponding computer-implemented method. The training may be performed using techniques known per se. For example, a gradient-based training may be performed such as stochastic gradient descent, e.g., using the Adam optimizer as disclosed in Kingma and Ba, "Adam: A Method for Stochastic Optimization" (available at https://arxiv.org/abs/1412.6980 and incorporated herein by reference). As is known, such optimization methods may be heuristic and/or arrive at a local optimum.

It will be appreciated by those skilled in the art that two or more of the above-mentioned embodiments, implementations, and/or optional aspects of the invention may be combined in any way deemed useful.

Modifications and variations of any system and/or any computer readable medium, which correspond to the described modifications and variations of a corresponding computer-implemented method, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

DETAILED DESCRIPTION OF EMBODIMENTS

Figure 1:
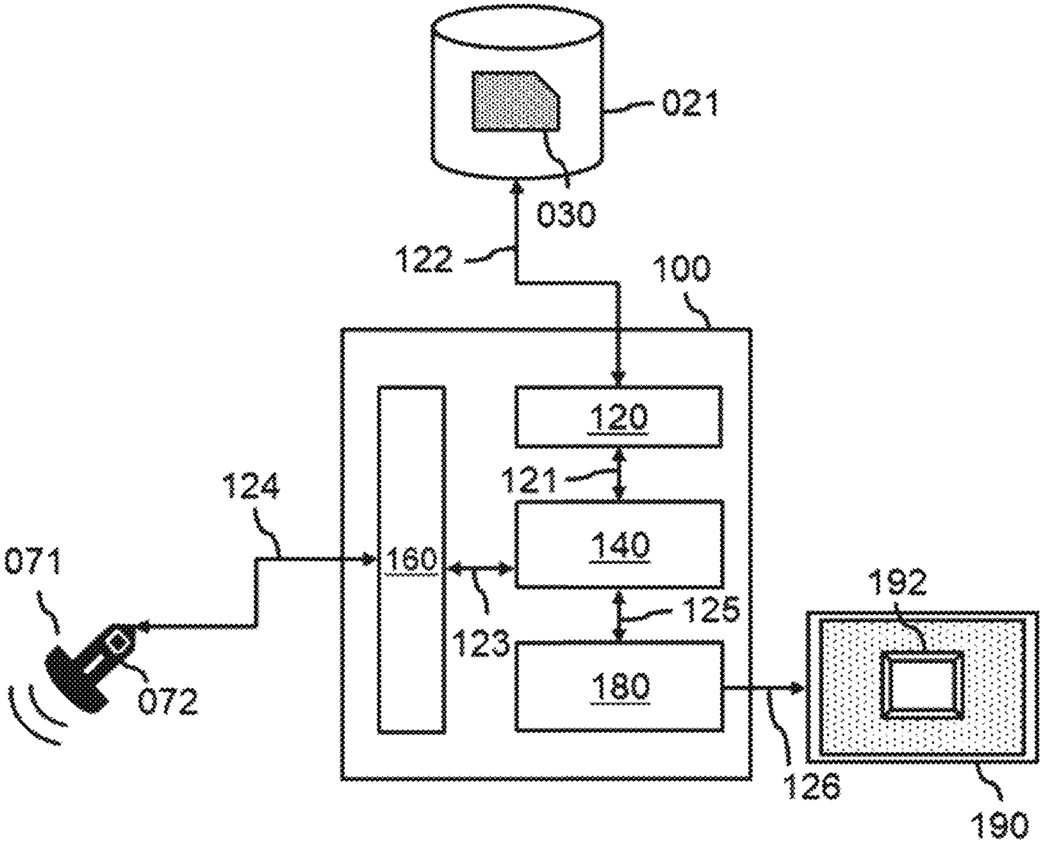
FIG. 1 shows an ultrasound fetal heart rate monitoring system.

FIG. 1 shows an ultrasound fetal heart rate monitoring system 100.

The system 100 may comprise a data interface 120 for accessing model data 030 representing a trained object detection model. The object detection model may be configured to localize a fetal heart in an ultrasound image. The model data 030 may comprise a set of trained parameters, for example, at least 10000 or at least 100000 parameters. For example, the model may be a neural network.

Neural networks are also known as artificial neural networks. In particular, the model may be a deep neural network or a convolutional neural network. In the case of a neural network, the set of parameters 030 may comprise weights of nodes of the neural network. For example, the number of layers of the model may be at least 5 or at least 10, and the number of nodes and/or weights may be at least 1000 or at least 10000. The data interface 120 may be for accessing additional information as described herein, e.g., model data representing a trained guidance model.

Model data representing the object detection model and/or guidance model may have been obtained by training the model, e.g., by system 100 itself or by another system with a similar hardware architecture, in particular by a system comprising a data interface and a processor system as described herein.

For example, as also illustrated in FIG. 1, the data interface 120 may be constituted by a data storage interface which may access the data 030 from a data storage 021. For example, the data storage interface 120 may be a memory interface or a persistent storage interface, e.g., a hard disk or an SSD interface, but also a personal, local or wide area network interface such as a Bluetooth, Zigbee or Wi-Fi interface or an ethernet or fibreoptic interface. The data storage 021 may be an internal data storage of the system 100, such as a hard drive or SSD, but also an external data storage, e.g., a network-accessible data storage. In some embodiments, respective data may each be accessed from a different data storage, e.g., via a different subsystem of the data storage interface 120. Each subsystem may be of a type as is described above for data storage interface 120.

The system 100 may further comprise a sensor interface 160 for obtaining sensor data 124 from an ultrasound probe 071. The ultrasound probe 071 is configured for placing on a maternal abdomen. The ultrasound probe 071 may be operable in an imaging mode and in a Doppler mode. Typically, the ultrasound probe 071 may operate in the imaging mode or in the Doppler mode, but not in both modes at the same time. The ultrasound probe 071 may comprise one or more transducers. For example, the transducers may be piezoelectric transducers, or the transducers may be CMUT transducers. The use of CMUT transducers is preferred because of lower production cost.

The transducers may be arranged in a configuration suitable for 2D and/or 3D ultrasound imaging phased array, e.g., in a 1D or 2D phased array configuration. For example, the number of transducers of the phased array can be at least two, at least ten, or least fifty. For example, the transducers may be arranged in a 1D phased array configuration, e.g., a linear phased array, e.g., comprising at least two, at least ten, or at least fifty transducers. As another example, the transducers may be arranged in a 2D phased array configuration, e.g., a matrix phased array. The matrix phased array can have at least ten or at least fifty transducers in both directions, for example, arranged in a rectangular pattern. Such a transducer pattern may be used for imaging, while also being usable in Doppler mode, for example, by using one particular transducer to produce one Doppler signal or using multiple respective transducers to produce multiple respective Doppler signals. In particular, the transducers are typically not arranged in a circular arrangement of piezoelectric elements with one piezoelectric element in the middle, since this arrangement does not work well for imaging. The ultrasound probe 071 may operate at a frequency of at least 1 MHz and/or at most 5 MHz, for example.

In the imaging mode, the ultrasound probe 071 may provide sensor data 124 representing an ultrasound image. The ultrasound image may represent amplitudes of echoes of an ultrasound signal transmitted by the transducer(s). In particular, the imaging mode may be a so-called B-mode. For example, a 1-dimensional phased array may be used to obtain a 2-dimensional image. It is also possible to use a 2-dimensional phased array to obtain a 3-dimensional image. It is also possible to use a 1dimensional phased array to obtain a 3-dimensional image, as disclosed for example in M. N. Senlik and H, Köymen, "Radiation Impedance of an Array of Circular Capacitive Micromachined Ultrasonic Transducers", IEEE Transactions on Ultrasonics, Ferroelectrics, and Frequency Control, vol. 57, no. 4, April 2010.

In the Doppler mode, a Doppler ultrasound signal may be obtained representing a velocity of a measurement volume. For example, the Doppler mode may be a pulsed wave (PW) Doppler mode in which ultrasound is alternatingly sent and transmitted, allowing to measure the velocity at a specified depth. By configuring the direction along with the signal is transmitted, e.g., by using beamforming, the Doppler ultrasound beam may be focused on a specific position. It is also possible to use a continuous wave (CW) Doppler mode. This typically does not allow to select a particular depth, although the direction of the signal may still be controlled.

Typically, both the imaging mode and the Doppler mode are served by the same set of transducers, but not at the same time, since the respective modes use respective different ultrasound signals. For example, in B-type imaging mode, beams may be transmitted by the respective transducers with respective phase differences to scan in a particular direction. In Doppler mode, for example, pulses may be sent by one transducer only, or the same pulse may be sent by multiple transducers at the same time. Accordingly, the ultrasound probe 071 may be configured, via a control signal 124 sent via the sensor interface 160 from the system 100 to the ultrasound probe 071, to operate in the imaging or the Doppler mode.

The Doppler ultrasound beam may be focused on a particular location, in particular the location at which the fetal heart is located by an object detection model as described herein. The beam may be focused by beamforming. This typically involves signal processing that may be implemented on ultrasound probe 071 itself or by processor subsystem 140 for example.

The ultrasound probe 071 may further comprise an orientation sensor, e.g., an IMU sensor. The processor subsystem 140 may be configured to obtain orientation data 124 indicating an orientation of the ultrasound probe via the sensor interface 160, e.g., comprising an angle of the sensor 071. This orientation data can be used to determine guidance information as described herein.

The system 100 may further comprise a processor subsystem 140 which may be configured to, during operation of the system 100, operate the ultrasound probe 071 in an imaging mode to obtain an ultrasound image 124 from the ultrasound probe 071. The processor subsystem 140 may be further configured to apply the object detection model 030 to the ultrasound image 124 to determine whether a fetal heart is located in a target region of the ultrasound image addressable by a Doppler mode of the ultrasound probe 071. The processor subsystem 140 may be further configured to, if the fetal heart rate is located in the target region, switch the ultrasound probe 071 to the Doppler mode; obtain a Doppler ultrasound signal 124 from the ultrasound probe; and compute the fetal heart rate from the Doppler ultrasound signal 124.

The system 100 may further comprise an output interface 180. Output interface 180 may be used for various outputs, including the fetal heart rate computed from the Doppler ultrasound signal; the ultrasound image; the located position of the fetal heart in the ultrasound image; a signal quality indication of the Doppler ultrasound signal; and/or guidance information. For example, the output interface may be an output interface to a rendering device, such as a display, a light source, a loudspeaker, a vibration motor, etc., which may be used to generate a sensory perceptible output signal which may be generated based on the information that is output. For example, as shown in the figure, the output interface may be to a display 190. In Doppler mode, e.g., the fetal heart rate 192 may be displayed, and/or an alert may be raised that the fetal heart rate is abnormal, and/or a signal quality indication of the Doppler ultrasound signal may be output. In the imaging mode, e.g., the ultrasound image, the position of the localized fetal body parts, and/or the guidance information may be shown, etc. As another example, the output interface may be constituted by the data interface 120, with said interface being in these embodiments an input/output ('IO') interface, via which the outputs, e.g., the fetal heart rate, may be stored in the data storage 021. It is also possible for the output interface to provide the outputs such as the determined fetal heart rate for further processing, e.g., the fetal heart rate may be provided to a fetal heart rate monitoring module operated by the processor subsystem 140.

The processor subsystem 140 may be further configured to determine a signal quality indication of the Doppler ultrasound signal 124. If the signal quality indication does not meet a predefined quality threshold, the ultrasound probe 071 may be switched back to the imaging mode via a control signal 124. Instead or in addition to using the signal quality indication to control the mode of the ultrasound probe, the processor subsystem 140 may also be configured to output the signal quality indication in a sensory-perceptible way to a user. This can for example be via output interface 180, e.g., on display 190, and/or it can be via a visual indicator 072 of the ultrasound probe, e.g., by one or more lights, e.g., with a colour, an intensity, and/or a number of lights of the visual indicator 072 being used to indicate the signal quality.

The system 100, ultrasound sensor 071, and/or display 190 can be arranged in various ways. For example, the system 100 and probe 071 may form a single device, e.g., with the processor subsystem 140 that applies the object detection model and determines the fetal heart rate being included in the ultrasound sensor 071 or fixedly connected to the sensor 071. The system 100 can also be implemented as a fetal monitor (connectable or connected to the probe 071), e.g., with a built-in or externally connectable display 190. The system 100 can also be implemented on the cloud, for example, with data being provided to a mobile device that provides shows the fetal heart rate on its display 190. System 100 may also itself be deployed on a mobile device, e.g., by providing its functionality as a mobile application.

More generally, each system described in this specification, including but not limited to the system 100 of FIG. 1, may be embodied as, or in, a single device or apparatus, such as a workstation or a server. The device may be an embedded device. The device or apparatus may comprise one or more microprocessors which execute appropriate software. For example, the processor subsystem of the respective system may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the processor subsystem of the respective system may be implemented in the device or apparatus in the form of programmable logic, e.g., as a Field-Programmable Gate Array (FPGA). In general, each functional unit of the respective system may be implemented in the form of a circuit. The respective system may also be implemented in a distributed manner, e.g., involving different devices or apparatuses, such as distributed local or cloud-based servers.

System 100 may instead or in addition be a training system for training the object detection model. Such a training system does not need to comprise a sensor interface 160 and/or output interface 180, and may use the data interface 120 to access the training data and/or model being trained, for instance.

Figure 2A:
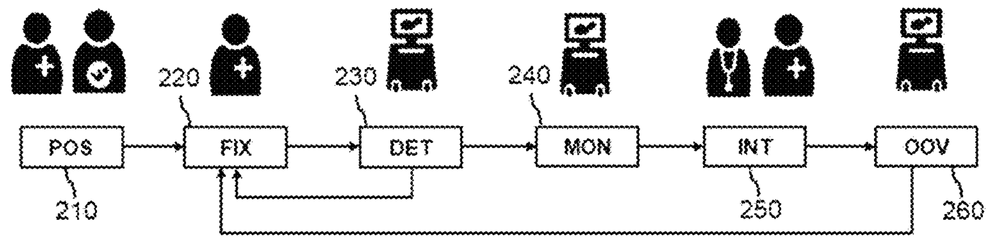
FIG. 2*a* shows a detailed example of how to monitor a fetal heart rate.

FIG. 2*a* shows a detailed, yet non-limiting, example of how to monitor a fetal heart rate using an ultrasound fetal heart rate monitoring system as described herein. The figure shows an overall flowchart showing several operations performed to detect fetal heart and plot the fetal heart rate in real time, e.g., on a mobile application. According to the figure, the fetal heart may be automatically detected from 2D ultrasound scan frames in real time, and pulse wave mode may be entered from 2D image mode to plot the fetal heart rate once the fetal heart is detected.

In position operation POS, 210, the ultrasound probe of the fetal heart rate monitoring system may be positioned, e.g., by a midwife, on the abdomen of the patient.

In fixing operation FIX, 220, the position of the ultrasound probe may be fixed and/or the ultrasound probe may be repositioned on the abdomen to obtain a trace. This can be done by the midwife, for example.

In detection operation DET, 230, the fetal heart may be detected and displayed, e.g., on a screen connected to the fetal heart rate monitoring system. A single/multiple piezo/CMUT sensor may be used to capture 2D ultrasound data from the initial location. An object detection algorithm may detect the fetal anatomy (e.g., fetal heart, head, spine and/or femur) on the ultrasound image taken from the initial location and may guide the user to a next location e.g., by suggesting a location to which to move the probe. IMU sensors may be used to provide the algorithm that detects the fetal heart with the angle of the sensor. If the fetal heart rate is not detected yet, the process may return to fixing FIX the ultrasound probe. The system may proceed to repeat detection operation DET. As also described elsewhere, optionally, if the fetal heart rate is not detected yet, information helping to locate the ultrasound probe to the correct location may be provided to the user, e.g., in the form of the ultrasound probe and/or the position(s) of located fetal organs, and/or in the form of guidance information.

Once the fetal heart is detected the probe may switch to Doppler mode and compute the fetal heart rate continuously. In particular, in monitoring operation MON, 240, Doppler mode may be enabled, and the fetal heart rate may be computed from the Doppler ultrasound signal by the fetal heart rate monitoring system. While in Doppler mode, a signal quality indication of the Doppler ultrasound signal may be determined as known per se. The signal quality indication may be output to a user, e.g., in the form of one or more lights or another visual indicator on the ultrasound probe itself.

In interpretation operation INT, 250, the trace and/or the fetal heart rate may be interpreted, e.g., by the midwife and/or a gynecologist.

In out-of-view operation OOV, 260, it may be determined that the fetal heart is out of view, e.g., the signal quality of the Doppler ultrasound signal may be insufficient to reliably determine the fetal heart rate, e.g., may fail to meet a predefined quality threshold. If this is the case, the fixing FIX of the ultrasound probe may be performed again, e.g., the probe may be switched back to imaging mode. Interestingly, switching to the imaging mode allows to help the user re-focus on the fetal heart so that the monitoring of the fetal heart rate can be continued. The quality threshold may be defined in such a way that, at the quality threshold, the fetal heart is generally still in range of the ultrasound images captured in the imaging mode. This way, if the signal quality drops below the threshold, it is possible to refocus relatively easy since the fetal heart can be indicated and/or guidance information based on the location of the fetal heart can be determined.

Figure 2B:
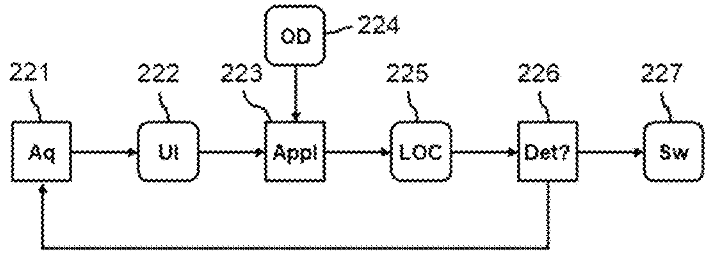
FIG. 2*b* shows a detailed example of how to switch an ultrasound probe from imaging mode to Doppler mode.

FIG. 2*b* shows a detailed, yet non-limiting, example of how to switch an ultrasound probe from imaging mode to Doppler mode.

In an acquisition operation Aq, 221, the ultrasound probe may be operated in an imaging mode to obtain an ultrasound image UI, 222, from the ultrasound probe. The ultrasound image may e.g., be at least 32×32 pixels, at least 128×128 pixels, or at least 512×512 pixels. The image may be greyscale.

In a model application operation Appl, 223, an object detection model OD, 224, may be applied to the ultrasound image UI to determine localization information LOC, 225, indicating whether a fetal heart is located in a target region of the ultrasound image addressable by a Doppler mode of the ultrasound probe.

The model OD may output the localization information LOC as is known for object detection models per se, e.g., in the form of class probabilities corresponding to one or more types of objects to be detected in combination with a location for the recognized object(s), e.g., a position and optionally also a size of the recognized object. The location may be represented e.g., as one or more coordinates in the ultrasound image, a bounding box, etc. Various object detection models are known per se and can be used.

In an embodiment, the object detection model comprises a neural network, in particular a deep neural network. In particular, the inventors achieved good results using the YOLO object detection model from J. Redmon et al., "You Only Look Once: Unified, Real-Time Object Detection" (available at https://arxiv.org/abs/1506.02640 and incorporated herein by reference). YOLO is a region proposal network which applies a single neural network to the full image to detect certain objects. This network divides the image into regions and predicts bounding boxes and probabilities for each region. YOLO divides the input image into a S×S grid. If the center of an object falls into a grid cell, that grid cell is responsible for detecting that object. Each grid cell predicts B bounding boxes and confidence scores for those boxes. The confidence scores reflect if indeed the box contains the object of interest and also the prediction accuracies. Each bounding box may comprise 5 predictions: x, y, w, h, and confidence. The (x, y) coordinates represent the center of the box relative to the bounds of the grid cell. The width (w) and height (h) are predicted relative to the whole image. The confidence level of the YOLO output is a regression which is trained to output the intersection of union (IOU) between output bounding box and ground truth bounding box. Other models based on the same principles can be used as well. As a concrete example, the YOLOv3 tiny model may be applied on 416×416 images.

Specifically, the object detection model OD may be trained on and applied to 2D fetal heart four chamber views. A positive training example may contain an axial view of the fetal heart, and can for example be curated from cine loops of 2D fetal scans. Planes that do not contain the fetal heart may be used as negative training examples. A training dataset may be created using these images by labelling them as fetal heart view, and annotating them with bounding boxes of the fetal heart, or as non fetal heart view. The images may be pre-processed to remove text annotations if needed. The annotation can be performed using the DarkLabel tool, for instance. Training can be performed using the Darknet deep learning framework. The inventors found that training for 4000 iterations with a batch size of 64 images yielded good results.

For example, a full training-test process may start with data and may comprise annotation; cleaning of annotated data; splitting of the data into training, validation, and test data, e.g., based on a patient ID; training of multiple models on training data by varying hyperparameters; validation of the models on validation data; finalization of the model with the highest validation accuracy; testing of the final model on unseen data; and computation of evaluation metrics.

Based on the localization information LOC it may be determined whether the fetal heart is located in a target region of the ultrasound image addressable by a Doppler mode of the ultrasound probe. For example, this may be the case if the fetal heart is recognized by the model with a confidence of at least a given threshold, and if the location at which the fetal heart is recognized, lies within the target region. The target region can for example correspond to the ultrasound image UI itself, or to a subregion of it. If the fetal heart rate is located in the target region, the ultrasound probe may be switched Sw, 227, to Doppler mode to start monitoring the fetal heart rate, as also discussed elsewhere, optionally using the localization information LOC to focus the Doppler ultrasound beam on the located position. As long as the fetal heart is not found to be in the target region, the acquiring Aq and subsequent steps may be repeated. Moreover, the localization information LOC may be used in various ways, in particular, the location may be output and/or used to determine guidance information to help the user to guide the ultrasound probe to the fetal heart, as also discussed in more detail elsewhere.

Figure 3:
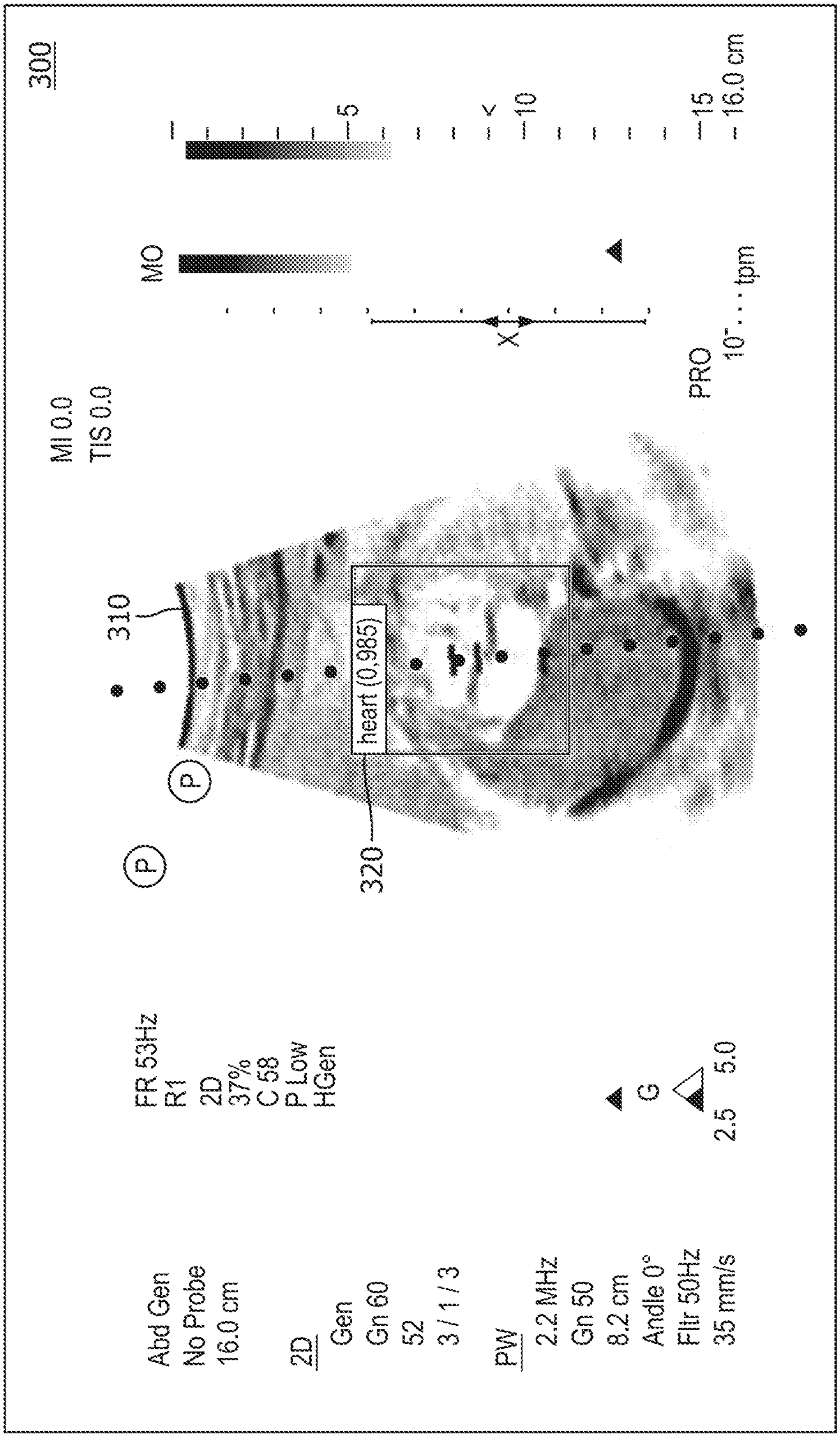
FIG. 3 shows a detailed example of localizing a fetal heart.

FIG. 3 shows a detailed, yet non-limiting, example of localizing a fetal heart. In this example, an object detection model is used that locates the fetal heart in an ultrasound image 310 by outputting a bounding box 320 in which the fetal heart is detected. The ultrasound image 300 and the bounding box 320 indicating the position of the fetal heart in the ultrasound image 310, are in this example shown in a user interface 300 to be shown on a display. As illustrated in the figure, optionally, the object detection model may additionally output a confidence value of the detection, that may be shown on the display as well, e.g., as a label (in this example: 0.985), as a color or line style of the bounding box, etc. If the fetal heart is not detected, e.g., the confidence value does not exceed a threshold, then the bounding box is typically not shown. The object detection model may be configured to detect additional fetal anatomies, for example, one or more of the fetal head, the fetal spine, and the fetal femur. Localizations for these additional anatomies, if detected, may be shown on the ultrasound image 310 as well.

Figure 4A:
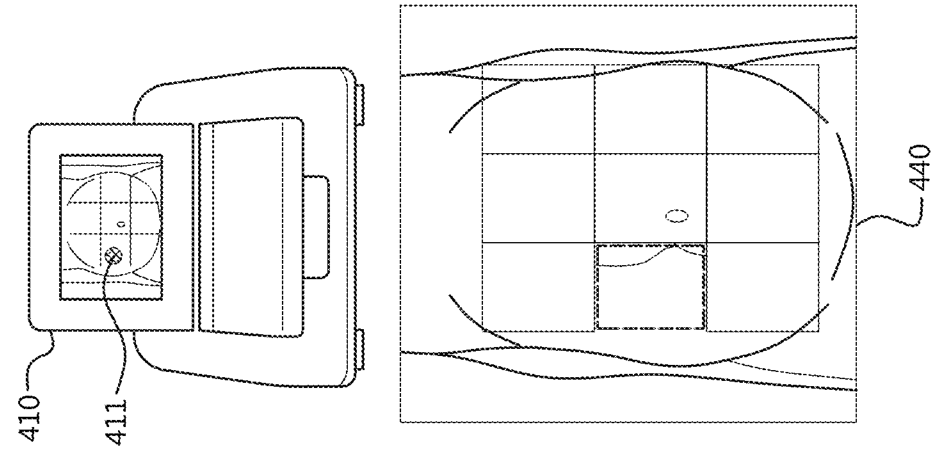
FIGS. 4*a*-4*c* show detailed examples of determining guidance information.
Figure 4B:
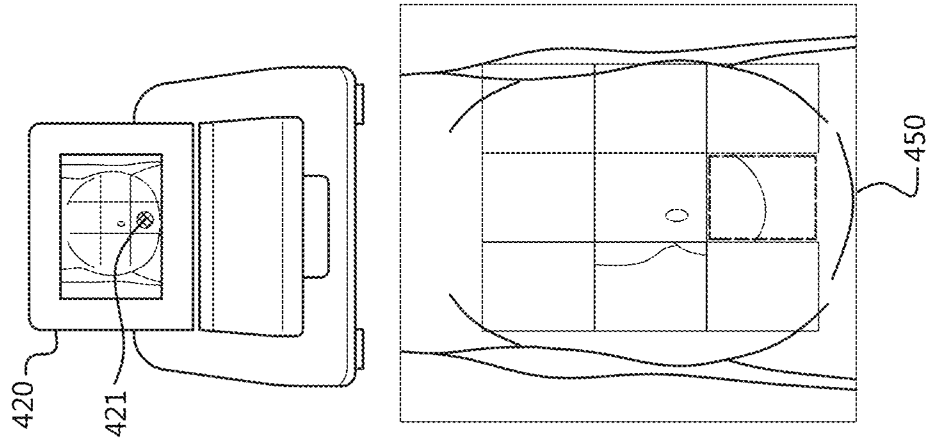
Figure 4C:
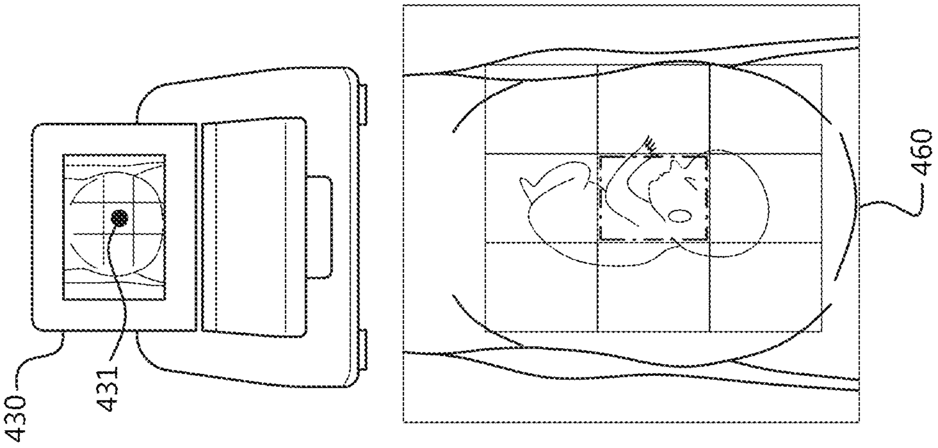

FIGS. 4*a*-4*c* show a detailed, yet non-limiting, example of determining guidance information for guiding an ultrasound probe to a fetal heart.

The guidance information may be determined, while the ultrasound sensor is in imaging mode, from locations of one or more fetal body parts recognized by an object detection model in an ultrasound image by the ultrasound sensor, as discussed e.g., with respect to FIG. 2*b*. The guidance information may additionally be based on the orientation of the ultrasound probe as determined by an IMU sensor or other orientation sensor. Interestingly, based on the orientation of the IMU sensor and using the geometry of the abdomen, the location of the IMU sensor on the abdomen may be determined. e.g., if the IMU sensor is oriented vertically it may be located in the middle of the abdomen; if it tilts to the left it may be located on the left side of the abdomen, etc. Other ways of determining the location of the ultrasound sensor on the abdomen, e.g., based on the ultrasound image, are possible as well, and can similarly be used to determine guidance information.

FIG. 4*a*-4*c* show a fetal heart rate monitoring system 410, 420, 430 with a display on which the guidance information is displayed in the form of a suggested position 411, 412, 413 to which to move the ultrasound probe. In this example, the suggested position is determined at the granularity of a suggested cell in a grid representing the abdomen. In this specific example, a 3×3 grid is used. The position is highlighted on a visualization of a maternal abdomen on which the location is augmented. The visualization can be a standard picture or illustration of a maternal abdomen. Thus, the guidance can be used without a need to store or show the ultrasound images that are used to determine the guidance, which can be beneficial as also mentioned elsewhere. The highlighting of the position may indicate a progress of the guidance. For example, on the fetal monitors shown in FIG.

4*a*-4*c*, a color of the highlighted position 411-431 in the example of FIG. 4*a* and FIG. 4*b* indicates that the fetal heart is not yet detected, whereas the color of the highlighting in FIG. 4*c* indicates that the fetal heart is detected. In the visualizations 440, 450, 460, an alternative highlighting of the position is shown, in the form of a style of a border of the suggested grid cell to which to move the probe. As shown in the figure, the border of the cell can have a different color than other cells and/or a thicker border.

The visualizations 440-460 also illustrate that an estimated placement of the fetus in the abdomen can be visualized. Also this can be based on a standard picture or illustration of a fetus. For example, the full fetus can be visualized, as shown in illustration 460, or a part of the fetus can be shown, as shown in illustrations 440, 450, e.g., corresponding to positions visited by the ultrasound probe and/or positions where the fetal anatomy is known based on the fetal anatomies localized so far. An example guidance procedure is illustrated in the figures. Using this guidance procedure may allow the user, e.g., the caregiver, to position the probe much faster towards the fetal heart (due to the automated object detection, which alleviates the need for manual palpation), while keeping in line with familiar existing protocols.

The guidance may start with proposing an initial position to place the ultrasound probe. As shown in FIG. 4*a*, the initial position can for example be the left middle of the abdomen. This position is often used in current protocols since it typically allows the fetal spine to be detected, allowing easier extrapolation of the remaining anatomy.

If the fetal spine is not detected, alternative initial position(s) may be proposed, e.g., right middle, top middle, bottom middle, etc.

If the fetal spine is detected but the fetal head is not yet detected, guidance information may be determined for guiding the ultrasound probe to an expected location of the fetal head. For example, an expected location of the fetal head may be determined under the assumption that the fetus is located with head down, leading to the suggested location 421 of FIG. 4*b*.

If the fetal head is not detected, alternative expected locations may be determined and suggested, e.g., based on the assumption that the fetus is located with head up, etc.

If the fetal spine and the fetal head are detected, guidance information may be determined for guiding the ultrasound probe to an expected location of the fetal heart. If the fetal spine and fetal head are located, an expected location of the fetal heart can be determined accurately based on normal fetal geometry. This is illustrated by suggestion 431 of FIG. 4*c* in which the fetal heart is suggested to be located in the middle cell of the grid.

If the fetal heart is not detected, an alternative location of the fetal heart can be determined, or the process can be restarted at the detection of the spine, for example. If the fetal heart is detected, then the system may switch to Doppler mode to monitor the fetal heart, as discussed. This can also happen while the guidance is still looking for the fetal spine or the fetal head. In this case it is possible to switch directly to Doppler mode, but if desired it is also possible to first continue the guidance process to also locate the fetal spine and head, so that the complete position and orientation of the fetus is determined. This information can for example be output to a user or used automatically, e.g., to predict the angle of progression of the fetal head during labor and/or delivery using a trained machine learning model.

To determine the guidance information, several approaches are possible. One possibility is to use an explicit geometric model of the fetal anatomy. This model can be relatively simple, e.g., the fetus may be modelled as a straight line representing the spine, ending at a sphere representing the fetal head. The location of the fetal heart may be determined with respect to determined locations of the line and sphere. An alternative is to use a machine learnable guidance model trained to output the guidance information, e.g., to output the cell in the grid of FIG. 4*a*-4*c*. For example, the guidance model may comprise respective models used to determine the locations of the fetal spine, the fetal head, and the fetal heart, respectively, in subsequent stages of the localization of the fetal heart. Another option is to applying a trained feature extractor to extract one or more features from the ultrasound image UI, and comparing the extracted features with a trained fetal image dataset for which guidance information is available. For example, a generic feature extractor may be used in this case.

Figure 5:
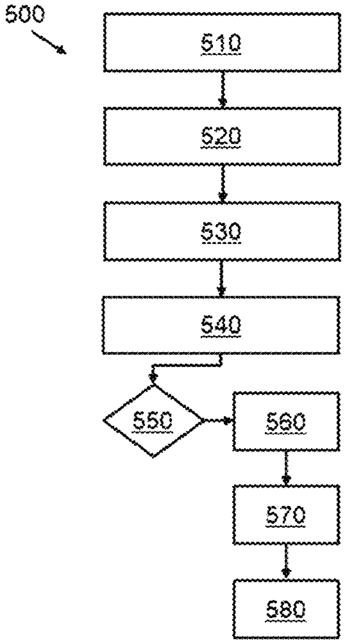
FIG. 5 shows a computer-implemented ultrasound fetal heart rate monitoring method.

FIG. 5 shows a block-diagram of computer-implemented method 500 for ultrasound fetal heart rate monitoring. The method 500 may correspond to an operation of the system 100 of FIG. 1. However, this is not a limitation, in that the method 500 may also be performed using another system, apparatus or device. The method 500 may comprise, in an operation titled "OBTAIN SENSOR DATA", obtaining 510 sensor data from an ultrasound probe to be placed on a maternal abdomen. The method 500 may comprise, in an operation titled "ACCESS OBJECT DETECTION MODEL", accessing 520 model data representing a trained object detection model. The object detection model may be configured to localize a fetal heart in an ultrasound image. The method 500 may comprise, in an operation titled "ULTRASOUND IMAGING", operating 530 the ultrasound probe in an imaging mode to obtain an ultrasound image from the ultrasound probe. The method 500 may comprise, in an operation titled "DETECT HEART", applying 540 the object detection model to determine whether a fetal heart is located in a position of the ultrasound image that is addressable by a Doppler mode of the ultrasound probe. The method 500 may comprise, in an operation titled "HEART DETECTED?", determining 550 if the fetal heart rate is located in the target region. The method 500 may comprise, if the fetal heart rate is detected, in an operation titled "SWITCH TO DOPPLER", switching 560 the ultrasound probe to the Doppler mode. The method 500 may further comprise, in an operation titled "OBTAIN DOPPLER SIGNAL", obtaining 570 a Doppler ultrasound signal from the ultrasound probe. The method 500 may further comprise, in an operation titled "MONITOR FHR", computing 580 the fetal heart rate from the Doppler ultrasound signal. It will be appreciated that, in general, the operations of method 500 of FIG. 5 may be performed in any suitable order, e.g., consecutively, simultaneously, or a combination thereof, subject to, where applicable, a particular order being necessitated, e.g., by input/output relations. The method may be combined with further steps, e.g., the object detection model and/or guidance model described herein may be trained prior to being applied. A separate computer-implemented method of training the object detection model and/or a guidance model is also envisaged.

Figure 6:
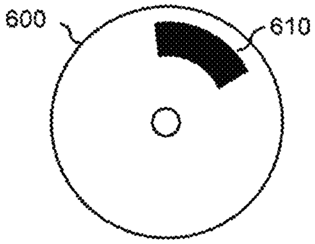
FIG. 6 shows a computer-readable medium comprising data.

The method(s) may be implemented on a computer as a computer implemented method, as dedicated hardware, or as a combination of both. As also illustrated in FIG. 6, instructions for the computer, e.g., executable code, may be stored on a computer readable medium 600, e.g., in the form of a series 610 of machine-readable physical marks and/or as a series of elements having different electrical, e.g., magnetic, or optical properties or values. The medium 600 may be transitory or non-transitory. Examples of computer readable mediums include memory devices, optical storage devices, integrated circuits, servers, online software, etc. FIG. 6 shows an optical disc 600. Alternatively, the computer readable medium 600 may comprise data 610 representing a trained object detection model and/or guidance model for use with the techniques described herein.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An ultrasound fetal heart rate monitoring system, comprising:

a sensor interface for obtaining sensor data from an ultrasound probe to be placed on a maternal abdomen;

a data interface for accessing model data representing a trained object detection model, wherein the object detection model is configured to localize a fetal heart in an ultrasound image;

a processor subsystem configured to:

operate the ultrasound probe in an imaging mode to obtain an ultrasound image from the ultrasound probe;

apply the object detection model to the ultrasound image to determine whether a fetal heart is located in a target region of the ultrasound image detectable by a Doppler mode of the ultrasound probe;

when the fetal heart is located outside of the target region: determine guidance information for guiding the ultrasound probe to an estimated position of the fetal heart from located positions of one or more fetal body parts localized by the object detection model, and to output determined guidance information to a display;

when a fetal spine is detected and a fetal head is not detected, determine guidance information for guiding the ultrasound probe to an expected location of the fetal head, and/or when the fetal spine and the fetal head are detected, determine guidance information for guiding the ultrasound probe to an expected location of the fetal heart; and when the fetal heart is located in the target region: switch the ultrasound probe to the Doppler mode; obtain a Doppler ultrasound signal from the ultrasound probe; and compute a fetal heart rate from the Doppler ultrasound signal.

2. The system of claim 1, wherein the system is configured to operate the ultrasound probe in the imaging mode or in the Doppler mode, but not in both modes at the same time.

3. The system of claim 1, wherein the processor subsystem is further configured to determine a signal quality indication of the Doppler ultrasound signal and, if the signal quality indication does not meet a predefined quality threshold, switch the ultrasound probe back to the imaging mode.

4. The system of claim 3, wherein the processor subsystem is configured to output the signal quality indication to a user.

5. The system of claim 4, wherein the outputting of the signal quality indication is of a visual indicator of the ultrasound probe.

6. The system of claim 1, wherein the ultrasound probe comprises one or more piezoelectric transducers and/or one or more capacitive micromachined ultrasonic transducer (CMUT) transducers.

7. The system of claim 1, wherein the processor subsystem is further configured to focus the Doppler ultrasound signal on the located position of the fetal heart.

8. The system of claim 1, further comprising an output interface to a display, wherein the processor subsystem is configured to show the position of the fetal heart in the ultrasound image on the display.

9. The system of claim 8, wherein the object detection model is further configured to localize one or more of the fetal head, the fetal spine, and a fetal femur, and wherein the processor subsystem is configured to show said localizations on the display.

10. The system of claim 9, wherein the object detection model is configured to localize one or more of the fetal head, the fetal spine, and the fetal femur, and the processor subsystem is configured to use said localizations to determine the guidance information.

11. The system of claim 10, wherein the ultrasound image is not shown on the display.

12. The system of claim 1, wherein the processor subsystem is further configured to obtain orientation data indicating an orientation of the ultrasound probe via the sensor interface, and to determine the location of the fetal heart and/or the guidance information using the orientation data.

13. A computer-implemented ultrasound fetal heart rate monitoring method, comprising:

obtaining sensor data from an ultrasound probe to be placed on a maternal abdomen;

accessing model data representing a trained object detection model, wherein the object detection model is configured to localize a fetal heart in an ultrasound image;

operating the ultrasound probe in an imaging mode to obtain an ultrasound image from the ultrasound probe;

applying the object detection model to determine whether a fetal heart is located in a position of the ultrasound image that is detectable by a Doppler mode of the ultrasound probe;

when the fetal heart is located outside of a target region: determining guidance information for guiding the ultrasound probe to an estimated position of the fetal heart from located positions of one or more fetal body parts localized by the object detection model, and outputting determined guidance information to a display;

when a fetal spine is detected and a fetal head is not detected, determining guidance information for guiding the ultrasound probe to an expected location of the fetal head, and/or when the fetal spine and the fetal head are detected, determin guidance information for guiding the ultrasound probe to an expected location of the fetal heart; and when the fetal heart rate is located in the target region: switching the ultrasound probe to the Doppler mode; obtaining a Doppler ultrasound signal from the ultrasound probe; and computing a fetal heart rate from the Doppler ultrasound signal.

14. A non-transitory computer-readable medium comprising data representing instructions which, when executed by a processor system, cause the processor system to perform the computer-implemented method according to claim 13.

* * * * *